United States Patent [19]
Klein

[11] Patent Number: 5,810,767
[45] Date of Patent: Sep. 22, 1998

[54] METHOD AND APPARATUS FOR PRESSURIZED INTRALUMINAL DRUG DELIVERY

[75] Inventor: Enrique J. Klein, Los Altos, Calif.

[73] Assignee: Localmed, Inc., Palo Alto, Calif.

[21] Appl. No.: 644,790

[22] Filed: May 10, 1996

Related U.S. Application Data

[63] Continuation-in-part of Ser. No. 241,428, May 11, 1994, Pat. No. 5,609,574.

[51] Int. Cl.⁶ .................................................. A61M 31/00
[52] U.S. Cl. .............................. 604/53; 604/96; 604/265; 604/280
[58] Field of Search ................................. 604/53, 96, 101, 604/104–106, 265–266, 280; 606/192, 194, 198

[56] References Cited

U.S. PATENT DOCUMENTS

| | | | |
|---|---|---|---|
| 4,636,195 | 1/1987 | Wolinsky | 604/53 |
| 4,824,436 | 4/1989 | Wolinsky | 604/53 |
| 4,911,163 | 3/1990 | Fina | 606/127 |
| 5,090,960 | 2/1992 | Don Michael | 604/101 |
| 5,176,638 | 1/1993 | Don Michael | 604/101 |
| 5,254,089 | 10/1993 | Wang | 604/96 |
| 5,306,249 | 4/1994 | Don Michael | 604/101 |
| 5,336,178 | 8/1994 | Kaplan et al. | 604/53 |
| 5,364,356 | 11/1994 | Hofling | 604/96 |
| 5,380,284 | 1/1995 | Don Michael | 601/101 |
| 5,415,636 | 5/1995 | Forman | 604/101 |
| 5,609,574 | 3/1997 | Kaplan et al. | 604/53 |
| 5,653,689 | 8/1997 | Buelna et al. | 604/96 |

FOREIGN PATENT DOCUMENTS

| | | | |
|---|---|---|---|
| 95/26777 | 10/1995 | WIPO | 604/53 |
| WO 95/26777 | 10/1995 | WIPO | A61M 31/00 |

OTHER PUBLICATIONS

Goldman, B. et al. "Influence of pressure on permeability of normal and diseased muscular arteries to horseradish peroxidase," *Atherosclerosis* (1987) 65:215–225.

*Primary Examiner*—Corrine M. McDermott
*Attorney, Agent, or Firm*—Townsend and Townsend and Crew LLP

[57] ABSTRACT

An intravascular catheter provides fluid infusion tubes over a balloon surface to form isolated reservoir pockets for delivering drugs intraluminally. The fluid infusion tubes will be arranged in a network which, upon balloon expansion, defines the isolated reservoir pockets between adjacent tubes. In one embodiment, the drug infusion tubes are formed as part of an expansible sleeve which is positioned over a separate balloon catheter for expansion. In another embodiment, the infusion tubes are disposed over a balloon of a balloon catheter.

37 Claims, 7 Drawing Sheets

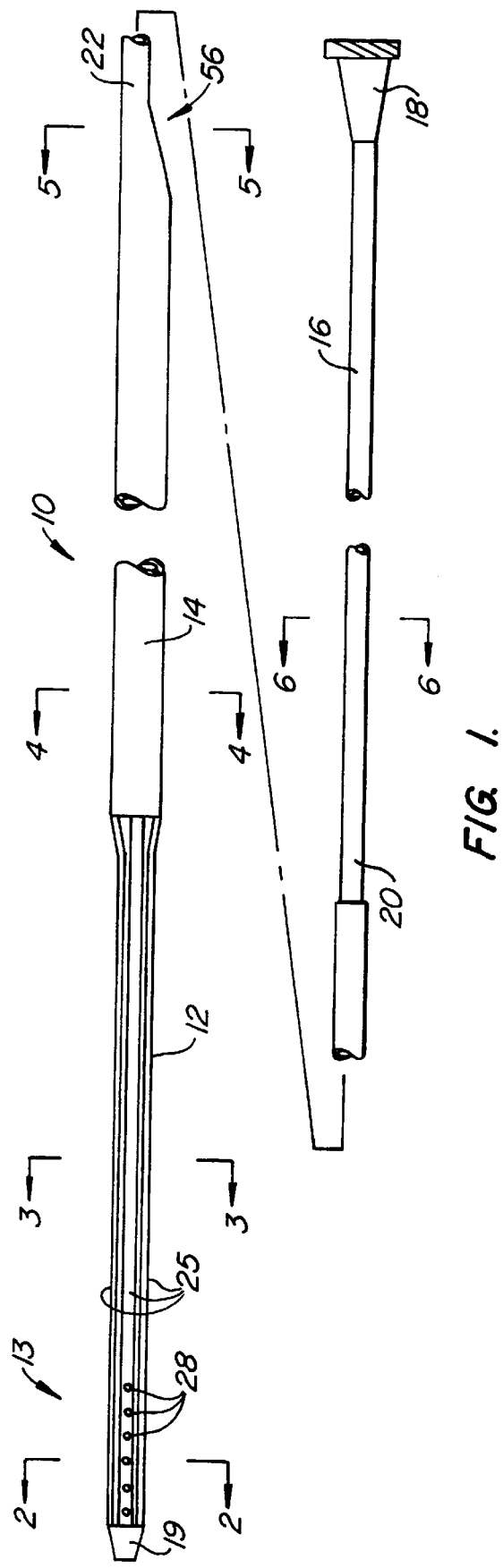
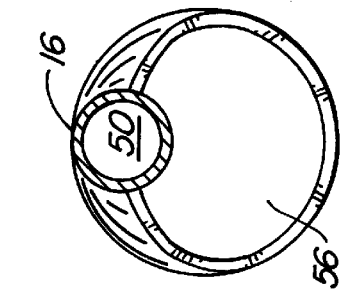
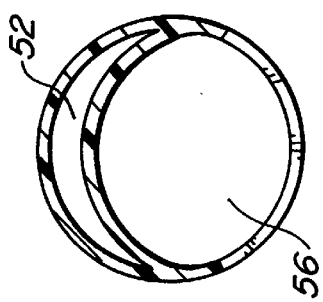
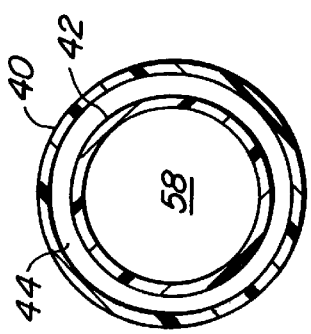
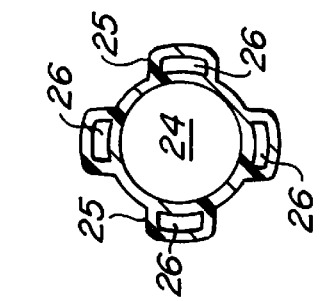
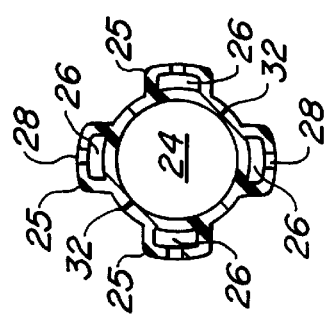

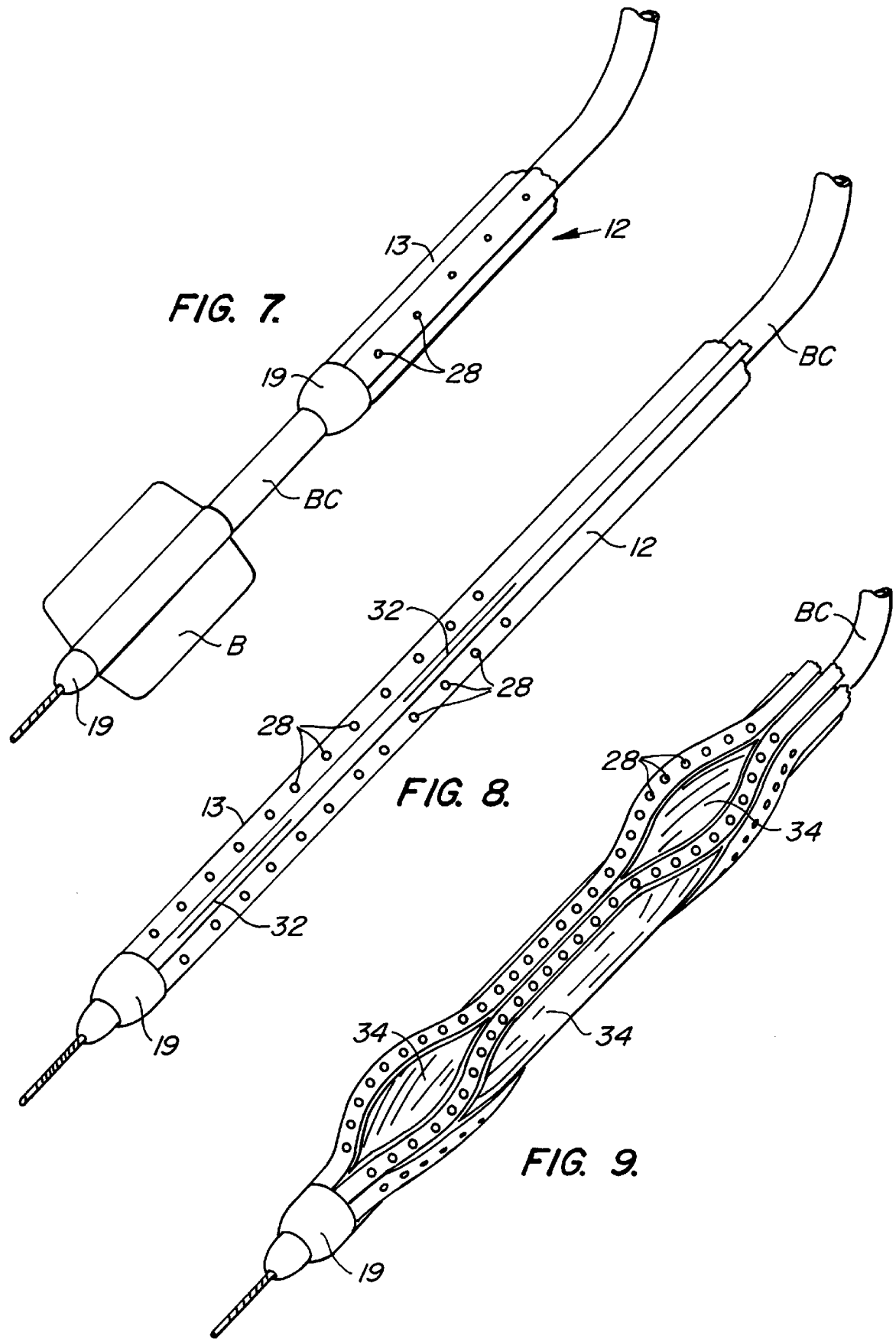

METHOD AND APPARATUS FOR PRESSURIZED INTRALUMINAL DRUG DELIVERY

CROSS-REFERENCE TO RELATED APPLICATIONS

The present application is a continuation-in-part of application Ser. No. 08/241,428, filed on May 11, 1994 now U.S. Pat. No. 5,609,574, the full disclosure of which is incorporated herein by reference.

BACKGROUND OF THE INVENTION

1. Field of the Invention

The present invention relates generally to apparatus and methods for infusing fluids within body lumens. More particularly, the present invention relates to the use and construction of an infusion catheter having a plurality of isolated fluid reservoir pockets for the pressurized intraluminal delivery of fluids.

Percutaneous transluminal angioplasty (PTA) procedures are widely used for treating stenotic atherosclerotic regions of a patient's vasculature to restore adequate blood flow. The catheter, having an expansible distal end usually in the form of an inflatable balloon, is positioned in the blood vessel at the stenotic site. The expansible end is expanded to dilate the vessel to restore adequate blood flow beyond the diseased region. While PTA has gained wide acceptance, it continues to be limited by two major problems: abrupt closure and restenosis.

The present invention is intended to address both problems and is particularly concerned with devices and methods for inhibiting restenosis by the localized delivery of fluid treatment agents. Such fluid treatment agents include anti-proliferative and anti-restenotic drugs intended specifically for post-angioplasty treatment, as well as anti-thrombotic, thrombolytic and fibrinolytic drugs useful for the acute treatment of atherosclerotic regions. The fluid treatment agents will include liquid drugs as well as solid drugs, including microcapsules and other controlled-release drug forms, present in a fluid dispersion. Restenosis refers to the re-narrowing of an artery after an initially successful angioplasty treatment. Restenosis afflicts approximately one in every three angioplasty patients and usually occurs within six months after the treatment. Patients suffering from restenosis will require further treatment. Many different strategies have been proposed to reduce the restenosis rate, including mechanical (e.g., prolonged balloon inflations during angioplasty, laser angioplasty, atherectomy, stenting and the like) and pharmacological, (e.g., the administration of calcium antagonists, ACE inhibitors, fish oils, steroids, anti-metabolic drugs, and the like).

Pharmacologic treatment can be either achieved systemically or via localized drug delivery. While systemic delivery is particularly easy to administer to the patient, it suffers from a number of disadvantages, primarily the need to provide higher total dosages, but also including the possibility of systemic toxicity and a lack of site specificity. The localized delivery of fluid and dispersed drugs, in contrast, limits the total drug dosage required, and provides site-specific activity where the drug has a much higher local concentration than is possible with systemic delivery, particularly when delivered intramurally.

A variety of specialized catheters have been developed to deliver drugs to a vascular treatment site following angioplasty or other interventional procedures. Most such drug delivery catheters are balloon angioplasty catheters which have been modified to release drugs in some manner from the balloon portion of the catheter. The need to provide such a dual function, however, necessarily leads to compromises in the design of both the balloon and drug delivery aspects of the catheter. In order to avoid such compromises, other "dedicated" drug delivery catheters have been designed for separate delivery to the treatment site following the initial interventional procedure. The use of separate catheters, however, has certain disadvantages. Mainly, the need to exchange the drug delivery catheter for the primary interventional catheter complicates and prolongs the procedure, increasing the time and cost to the patient. Additionally, many prior drug delivery catheters have been somewhat complex and costly, further increasing the cost of the procedure, have had limited effectiveness, and/or have required long infusion times (up to 30 minutes). It would thus be desirable to provide improved drug delivery catheters which overcome some or all of these problems.

An improved catheter and method for delivering treatment agents to an angioplasty treatment site is described is U.S. Pat. No. 5,336,178. Catheters employing the teachings of the patent have been developed under the tradename Kaplan-Simpson InfusaSleeve™ by LocalMed, Inc., Palo Alto, Calif. These devices are sleeve catheters having a plurality of drug infusion lumens formed over their entire lengths. A distal portion of the catheter is radially expansible and may be positioned over the balloon of an angioplasty balloon catheter in order to engage drug delivery ports against the vessel wall by inflation of the balloon. Following angioplasty with a conventional angioplasty catheter, the expansible region of the drug infusion lumens of the sleeve catheter are aligned over the balloon of the same angioplasty catheter. The balloon is then used to expand the infusion lumens at the treatment site, and drug is introduced under pressure through the infusion lumens.

Another approach for intravascular drug delivery relies on the creation of isolated volumes or "reservoirs" between pairs of spaced-apart balloons on a catheter. A drug can be delivered to the reservoir at a preselected pressure, typically in the range from 3 psi to 10 psi, and pressurization of the drug can be maintained for time periods on the order of minutes. Such drug delivery techniques have been shown to be effective at achieving intramural penetration of the blood vessel wall. While advantageous for that reason, such methods and catheters have not been practical since both drug and pressure can be lost through side branches of the vasculature. Also, the need to remove blood from the isolated volume created by spaced-apart balloons prior to drug infusion can be difficult or impossible with present catheter designs.

For these reasons it would be desirable to provide improved methods and catheters for the intramural delivery of drugs by the creation of a multiplicity of small pressurized reservoirs of the drugs. It would be particularly desirable if the methods and catheters could be used in regions of the vasculature having side branches without substantial loss of pressure and/or drug. It would be still further desirable if the pressurized reservoirs could be created using a sleeve catheter of the type disclosed above as well as with balloon catheters. Catheters of the present invention should further be manufacturable at relatively low cost and should optionally address at least some of the objectives and problems identified above.

2. Description of the Background Art

Catheters having pairs of spaced-apart balloons for defining a pressurized fluid delivery chamber therebetween are described in U.S. Pat. Nos. 4,636,195 and 4,824,436. Catheters having similar spaced-apart balloons are presently being manufactured by World Medical Manufacturing Corporation, Sunrise, Fla. The influence of pressure on artery permeability is described in Goldman et al. (1987) *Atherosclerosis* 65:215-225. Other relevant patents include U.S. Pat. Nos. 5,415,636; 5,380,284; 5,306,249; 5,254,089; 5,176,638; 5,090,960; and 4,911,163.

United States patent applications Serial Nos. 08/473,800, filed Jun. 7, 1995, and Ser. No. 08/551,932, filed on Oct. 23, 1995, have related disclosures. The full disclosures of each of these applications are incorporated herein by reference.

WO 95/26777 is a published PCT application which claims priority from U.S. Ser. No. 08/241,428 which is a parent to the present application. FIGS. 15 and 16 illustrate a catheter which may be used to practice the method of the present invention.

SUMMARY OF THE INVENTION

The present invention provides devices and methods for the delivery of therapeutic and other fluids to a target site within a body lumen. While the methods and devices will be particularly useful for the intravascular delivery of anti-restenotic, anti-proliferative, thrombolytic, fibrinolytic, and other agents useful in connection with angioplasty treatment in a patient's coronary vasculature, they will also find use for the delivery of a wide variety of other agents to other body lumens.

Methods according to the present invention rely on expanding a balloon within a body lumen, where the balloon has an outer peripheral surface which engages an inner wall portion of the body lumen, usually a diseased inner wall of a coronary or other artery. A plurality of isolated fluid reservoir pockets are provided between the outer peripheral surface of the balloon and the inner wall portion of the body lumen. Fluid is then delivered to said isolated reservoir pockets under pressure, typically in the range from 3 psi to 10 psi. By providing a relatively large number of reservoir pockets, typically from 6 to 64, usually from 10 to 32, and preferably from 10 to 24, fluid loss through side branches is minimized. That is, usually fluid loss to a single side branch is limited to one or at most two of the isolated reservoir pockets, and pressure can be maintained in the remaining reservoir pockets without substantial compromise.

Usually, the isolated pockets will each have an area in the range from 10 mm$^2$ to 60 mm$^2$, preferably from 15 mm$^2$ to 30 mm$^2$. With corresponding volumes in the range from 2.5 $\mu$l to 15 $\mu$l, preferably from 3.5 $\mu$l to 7 $\mu$l. The isolated pockets will preferably be substantially uniformly distributed over the outer peripheral surface of the balloon, and the fluid is delivered to the isolated pockets through one or more flow-limiting infusion port(s), where the sum of the cross-sectional areas of the infusion ports is a fraction of the cross-sectional area of the infusion lumen leading to said port(s), typically being in the range from 5% to 20% of the luminal cross-sectional area. Such flow limitation helps assure that excessive fluid loss will not occur through any one isolated pocket.

The providing step typically comprises disposing a network of fluid infusion tubes between the balloon and the inner wall portion of the body lumen, where the fluid infusion tubes are interconnected to form the isolated reservoir pockets. In an exemplary embodiment, the fluid infusion tubes will be interconnected, usually with reinforcement ribs, to form a diamond pattern when the balloon is expanded. In a preferred embodiment, the network of fluid infusion tubes is disposed on an expansible sleeve which is positioned between the balloon and the luminal wall portion prior to balloon expansion. Alternatively, the network of fluid infusion tubes may be provided as an integral component of a balloon catheter.

In a first aspect of the apparatus of the present invention, an infusion catheter for intramural drug delivery comprises a catheter body having a proximal end, a distal end, and a radially expansible segment disposed at the distal end of the catheter body. The radially expansible segment includes a network of fluid infusion tubes which are interconnected to form a plurality of isolated pockets when the segment is expanded against a body lumen wall. The fluid infusion tubes are provided with infusion ports for delivering fluids into the isolated pockets. Typically, the infusion port(s) have a total cross-sectional areas in the range set forth above.

In a preferred embodiment, the radially expansible segment comprises a sleeve which has a central receptacle capable of receiving a balloon, such as a conventional angioplasty balloon, to be deployed therein. Alternatively, the catheter may comprise a balloon, where the network of infusion tubes is separately or integrally formed over the outer peripheral surface of the balloon.

In both the sleeve and balloon catheter embodiments, the number and size of the isolated pockets or reservoirs in the network of infusion tubes will typically in the ranges set forth above. Optionally, the radially expansible segment of the catheter may further include reinforcing ribs which are arranged over the expansible segment to improve the column strength and pushability thereof. Typically, the fluid infusion tubes and optionally reinforcing ribs are interconnected in a manner which forms a diamond pattern when the segment is expanded.

In a second aspect of the apparatus of the present invention, an infusion catheter comprises a catheter body having a proximal end, a distal end, and a radially expansible sleeve disposed at the distal end of the catheter body. In an exemplary embodiment, the catheter body comprises a shaft having a fluid delivery lumen therethrough. The catheter further comprises a manifold structure disposed between the shaft and the network of infusion tubes, where the manifold distributes fluid from the fluid delivery lumen to the fluid infusion tubes. The remaining dimensions and other characteristics of the second embodiment are generally as set forth above.

BRIEF DESCRIPTION OF THE DRAWINGS

FIG. 1 is a side view of an infusion catheter constructed with the principles of the present invention.

FIG. 2 is a cross-sectional view taken along line 2—2 in FIG. 1.

FIG. 3 is a cross-sectional view taken along line 3—3 in FIG. 1.

FIG. 4 is a cross-sectional view taken along line 4—4 in FIG. 1.

FIG. 5 is a cross-sectional view taken along line 5—5 in FIG. 1.

FIG. 6 is a cross-sectional view taken along line 6—6 in FIG. 1.

FIG. 7 is a detailed view of the distal end of the catheter of FIG. 1 positioned over the shaft of a balloon angioplasty catheter just proximal to an uninflated balloon.

FIG. 8 is a detailed view of the distal end of the catheter of FIG. 1, similar to FIG. 7, shown with the balloon receptacle of the catheter positioned over the uninflated balloon of the balloon catheter.

FIG. 9 is a detailed view of the distal end of the catheter of FIG. 1, similar to FIGS. 7 and 8, shown with the balloon receptacle positioned over an inflated balloon on the balloon angioplasty catheter.

DESCRIPTION OF THE SPECIFIC EMBODIMENTS

Figure 10:
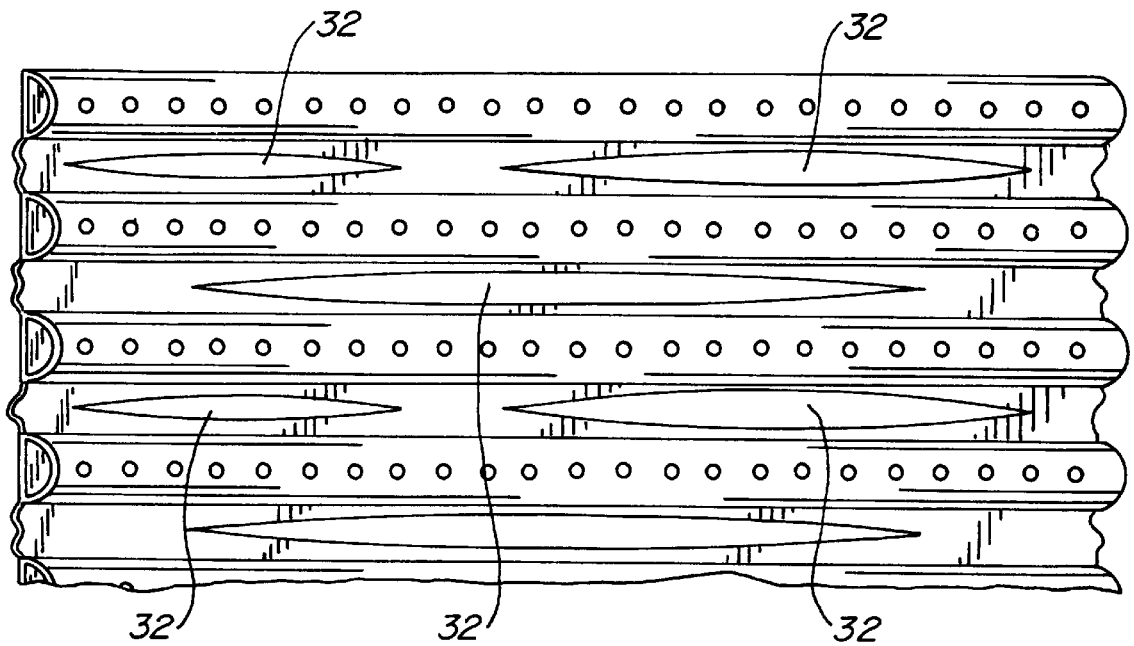
FIG. 10 is a planar projection of the infusion array of FIG. 9, where the tubular array has been "unrolled" to show a pattern of splits between adjacent pairs of infusion tubes.

The present invention provides apparatus and methods for infusing therapeutic, diagnostic, and other fluid media to target sites within a patient body lumen, such as a blood vessel, usually a coronary or other artery. The fluid media which may be delivered include liquids, e.g., where the drug is itself in liquid form, and dispersions, where the drug may be in solid form (optionally being incorporated in microcapsules or other controlled-release delivery systems, including liposomes and other vesicles) and is dispersed in a suitable liquid carrier. The procedures will be performed "intraluminally," by which it is meant that the procedures occur at a target site within a body lumen, usually being within the patient vasculature, more usually being within the arterial system, including the coronary arteries, the peripheral arteries, and the cerebral arteries. The methods and apparatus of the present invention will find their greatest use in the intramural delivery of therapeutic fluid agents, such as anti-restenotic drugs, anti-thrombotic drugs, thrombolytic agents, fibrinolytic agents, anti-proliferative agents, and the like, to sites within the coronary vasculature, where an infusion catheter according to the present invention is introduced in tandem with or as part of a balloon catheter. The methods and apparatus of the present invention, however, are not limited to use in the vascular system, and may also be advantageously employed in other body lumens, including the urethra (e.g., to treat benign prostatic hypertrophy, prostatitis, and adenocarcinoma), the fallopian tubes (e.g., to treat strictures), brain parenchyma (to treat Parkinson's disease), and the like. The methods and apparatus of the present invention are not limited to the delivery of conventional drugs, and may also be used to deliver genes, nucleic acids, DNA constructs, and the like, usually present in liposomes or other carriers, intended for gene therapy and other therapeutic approaches.

The "target site" within the body lumen will usually be diseased or suspected of being diseased. In the case of vascular treatment, exemplary target sites will be stenotic regions where blood flow is restricted as a result of the formation of atheroma or plaque. Diseased sites within other body lumens are well known and described in the medical literature.

A sleeve catheter embodiment of the infusion catheters of the present invention will be used in combination with radially expansible catheters, such as balloon catheters, of the type intended to dilate body lumens, such as blood vessels. For example, angioplasty devices and catheters suitable for use in the present invention are described in U.S. Pat. Nos. 5,041,089; 4,762,129; 4,775,371; 4,323,071 and 4,292,974, the full disclosures of which are incorporated herein by reference. Suitable angioplasty catheters are available commercially from suppliers such as Advanced Cardiovascular Systems, Inc., Temecula, Calif.; Cordis Corp., Miami, Fla.; Boston Scientific Co., Inc., Natic, Massachusetts, and others.

The sleeve catheter embodiments of the infusion catheters of the present invention will usually comprise a radially expansible sleeve member mounted on the distal end of a shaft having an infusion fluid delivery lumen therein. The infusion sleeve will have a central receptacle for receiving the balloon or other expansible device on the conventional catheter as well as a plurality of fluid infusion tubes forming or disposed over its outer surface or within its walls. The sleeve will be radially expansible over a portion which includes fluid infusion ports which are thus able to release fluids supplied to the lumens when the balloon or other expansion device is expanded therein. The infusion sleeve will be sufficiently large to receive a desired size of balloon or other expansible catheter and to accommodate the fluid infusion lumens on its upper surface or within its walls. Radial expansibility can be provided in a number of ways. In the exemplary embodiments, the sleeve will be axially split in order to allow radial expansion. Such expansibility can also be provided by use of an elastic material, use of an expansible braid material, use of a folded compliant or non-compliant material which will unfold when a balloon is inflated therein, and the like. A number of specific designs for providing expansible balloon receptacles are described in copending application Ser. No. 08/401,541, the full disclosure which is incorporated herein by reference.

The radially expansible portion of the sleeve will usually have a length sufficient to extend over the entire length of the balloon when expanded. Preferably, the sleeve will have a length which is greater than that of the balloon in order to facilitate manipulation of the sleeve over the catheter shaft, as described in more detail herein below. Thus, the length of the sleeve will usually be at least 2.5 cm, typically being from 2.5 cm to 50 cm, usually being from 5 cm to 25 cm. The diameter of the sleeve will be sufficiently small to pass through a guide catheter, past the coronary ostium, and into the coronary vasculature, typically being below 2 mm, usually being in the range from 1.5 mm to 2 mm.

The fluid infusion tubes will usually form or extend over at least a portion of the radially expansible portion of the sleeve, usually extending over that portion which is radially expanded by the balloon catheter. To simplify construction, and in particular to position the transition between the sleeve and the shaft of the infusion catheter within the guiding catheter during use, the infusion lumens will typically extend over at least most of the length of the infusion sleeve, usually being at least 2.5 cm in length, typically having a length in the range between 2.5 cm to 50 cm, and most usually having a length in the range from 10 cm to 25 cm. The infusion ports which are formed in the sleeve to release infusate from the infusion lumens will usually extend only over a distal portion of the sleeve, normally being disposed only over the radially expansive portion which lies over the balloon to be inflated.

The fluid infusion tubes will be arranged so that, upon expansion of the sleeve, they will define a plurality of isolated fluid reservoir pockets therein. That is, the infusion tubes (optionally in combination with the reinforcement ribs described below), will define walls or barriers which create the isolated fluid-containing pockets when engaged against the luminal wall. Usually, adjacent fluid infusion tubes will be split or separated from each other along axially staggered lines. In that way, expansion of the expansible portion of the sleeve will create a plurality of diamond-shaped reservoir pockets between adjacent fluid infusion tubes. Optionally, the radially expansible sleeve may further comprise reinforcement ribs positioned between adjacent fluid infusion tubes. The reinforcement ribs will enhance the pushability of the distal end of the sleeve catheter and may also help define the isolated reservoir pockets upon expansion of the sleeve. Specific examples of such structures will be described in connection with the drawings below.

The diameter of the shaft portion of the infusion catheter will be smaller than that of the radially expansible infusion sleeve, typically being below 1 mm, preferably being below 0.8 mm. In a first specific embodiment, the shaft may be formed from a simple tubular member having sufficient axial and flexural strength to permit manipulation of the catheter within the body lumen. Exemplary tubular structures include hypo tube and other metal tubes having circular or non-circular cross-sections, as described in more detail below. Alternatively, the shaft structure may comprise extruded polymeric tubes having one or more lumens, where at least one of the tubes is reinforced with an internal rod. Such structures are advantageous since the shafts can be configured to have variable flexibility by using tapered reinforcement rods. In particular, such rods can be tapered to be highly flexible near their distal ends, and in some cases can be extended into at least a proximal portion of the radially expansible sleeve structure in order to better connect the adjacent structures and enhance the pushability of the entire catheter. The fluid delivery lumen in the shaft will typically have a cross sectional area in the range from 0.2 mm$^2$ to 0.5 mm$^2$, preferably from 0.25 mm$^2$ to 0.35 mm$^2$. The shaft will typically have a length in the range from 90 cm to 150 cm, preferably from 100 cm to 125 cm.

The radially expansible infusion sleeve may be composed of a wide variety of biologically compatible materials, typically being formed from natural or synthetic polymers, such as polyamide (nylon), polyvinyl chloride, polyurethanes, polyesters, polyethylenes, and polytetrafluoroethylenes (PTFE's). A preferred material for the sleeve is polyamide (nylon).

The infusion sleeves will usually be non-compliant, and may optionally be reinforced to maintain patency of the infusion tubes and lumens during use. Usually, the sleeve structures will be formed by conventional extrusion of the desired polymeric material, forming both the central receptacle and the infusion lumens simultaneously. Cross-sectional areas and geometries of the infusion lumens and central receptacle may be controlled precisely using precision tooling mounted in a high precision extruder. With four infusion tubes, each lumen will typically have cross-sectional areas in the range from 0.05 mm$^2$ to 0.15 mm$^2$, usually from 0.08 mm$^2$ to 0.12 mm$^2$, and total (combined) cross-sectional areas in the range from 0.2 mm$^2$ to 0.6 mm$^2$, usually from 0.32 mm$^2$ to 0.48 mm$^2$.

At least a portion of the infusion sleeve will be radially expansible. Typically, the sleeve will be formed as a tubular section with the infusion lumens being formed during the extrusion process. The infusion lumens can be formed as protrusions or projections formed "over" a relatively thin tubular web or wall, typically having a thickness from about 0.05 mm to 0.1 mm. Alternatively, the tubular web or wall may be formed as a relatively thick structure, typically having a thickness from 0.2 mm to 0.4 mm, where the infusion lumens are formed within the wall without projecting or protruding above the outer surface of the wall. In either case, the radial expansibility will typically be provided by segmentally splitting the tubular wall or web over a length generally equal to the length which is desired to be expansible. Such splitting will be performed after the initial extrusion. Alternative structures which provide radial expansibility are described elsewhere in this application.

The fluid delivery lumen in the shaft will be connected to the individual fluid infusion lumens in the infusion sleeve by a manifold structure disposed at the junction between the shaft and the infusion sleeve. Typically, the manifold will form a transition from the single lumen of the shaft through an annular lumen and into the axial, individual lumens of the infusion sleeve. For example, the extrusion of the infusion sleeve may first have the infusion lumens removed from the proximal end thereof. Such removal leaves lumen entrances at the proximal end of the infusion lumens. By then placing a cover sheath over the proximal end of the infusion sleeve, and properly heat-shrinking the assembly using internal mandrels, a transition from an annular lumen to the individual lumens can be formed. Similarly, the transition from the single lumen of the shaft to the annular lumen can be formed at the proximal end of the sleeve structure. Usually, a balloon entry port into the central lumen will be formed at the same time during the fabrication process.

In the preferred embodiment, a manifold structure provides the necessary transition between the lumen(s) in the shaft, typically one, but in some cases two, to a larger number of lumens in the infusion tubes on the sleeve, typically at least four, often six, and sometimes as many as eight or more.

Referring now to FIGS. 1–6, an exemplary infusion catheter 10 constructed in accordance with the principles of the present invention will be described. The infusion catheter 10 comprises a radially expansible infusion sleeve 12, a radially expansible portion 13 within the sleeve 12, a manifold section 14, and a shaft 16. A hub 18 is attached to the proximal end of the shaft 16 and may be connected to a source of infusion fluid, such as a syringe, pump, or the like. An atraumatic tip 19 is secured to the distal end of the sleeve 12. Distal end 20 of the shaft is secured within a proximal tubular extension 22 of the manifold structure 14. As illustrated in FIGS. 1–6, the shaft 16 is a metal hypo tube having a circular cross-sectional area. The length of the shaft will depend on the length of the other portions of the catheter 10, with the overall length of the catheter typically being about 90 to 150 cm for coronary applications introduced through the femoral artery, as described in more detail below.

The radially expansible infusion sleeve 12 comprises a central receptacle 24 (FIGS. 2 and 3) and four infusion lumens 26. Infusion ports 28 are formed in infusion tubes 25 over the distal-most 2.5 to 10 cm of the expansible portion 13 of the sleeve 12. Usually, the expansible portion 13 of the sleeve is axially split along lines 32 (FIG. 2) in a staggered pattern (FIG. 10) to permit radial expansion and formation of isolated reservoir pockets 34, as illustrated in FIG. 9 described below. The distal ends of the lumens 26 will be sealed, typically by the tip 19.

The manifold structure 14 comprises an outer sheath or tube 40 coaxially received over an inner tube 42. Annular lumen 44 directs infusate into the infusion lumens 26. The annular lumen 44 is connected to lumen 50 and shaft 16 (FIG. 6) by a crescent-shaped transition lumen region 52 (FIG. 5) which is formed near the balloon catheter entry port 56. The balloon entry port 56 opens into a catheter lumen 58, which in turn leads into the balloon receptacle 24, typically having a cross-sectional area in the range from 0.5 mm$^2$ to 2 mm$^2$, typically about 1.25 mm$^2$.

Referring now to FIGS. 7–10, a balloon catheter BC having an inflatable balloon B may be introduced through entry port 56 so that the balloon B extends outward through the distal tip of the sleeve 12. The balloon may then be inflated and deflated while the infusion sleeve 12 remains retracted. After the balloon B is deflated, the sleeve 12 may be advanced distally over the balloon, as illustrated in FIG. 8. By then inflating the balloon, the expansible portion 13 of the sleeve 12 will be expanded, as illustrated in FIG. 9, forming a plurality of isolated fluid reservoir pockets 34.

As illustrated in FIGS. 1–10, infusion ports 28 are located on the radially outward surface of the infusion tubes 25. It will be appreciated that in such embodiments the fluids introduced through ports 28 will both penetrate the adjacent luminal wall as well as flow into the pocket reservoirs 34 where they will accumulate at a pressure defined by the fluid delivery pressure through the ports 28. In many cases, it will be preferred to orient infusion ports in the infusion tubes laterally outward in order to directly deliver fluid into the pocket reservoirs. Such an embodiment is illustrated in FIGS. 11–14.

Figure 12:
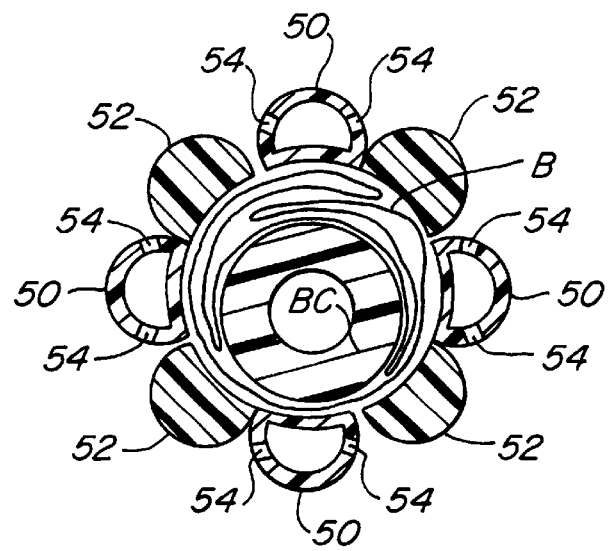
FIG. 12 is a cross-sectional view of the catheter of FIG. 11, shown in its radially collapsed configuration.
Figure 11:
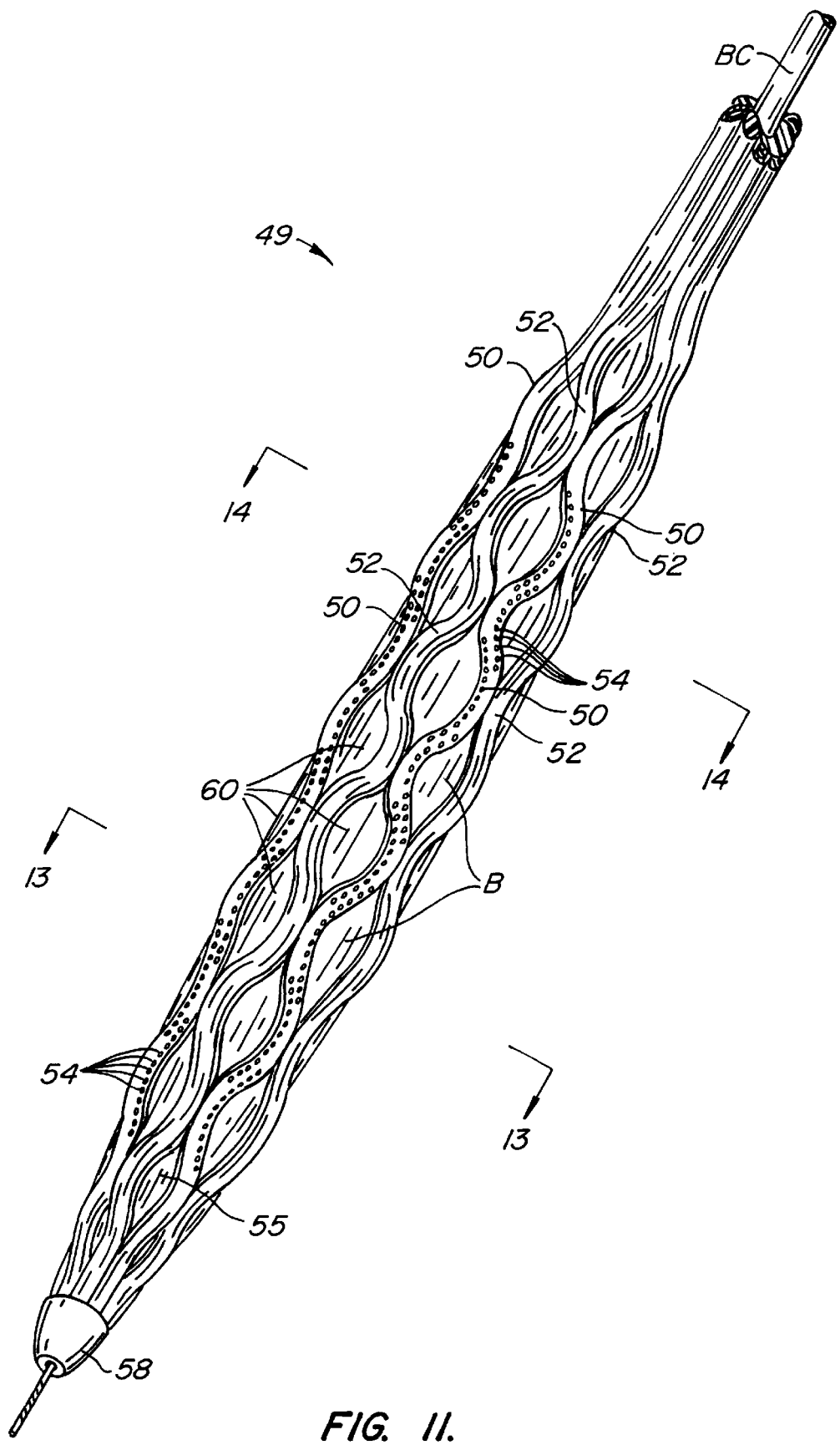
FIG. 11 is a perspective view of the distal end of an alternative sleeve catheter embodiment, shown in its radially expanded configuration.
Figure 13:
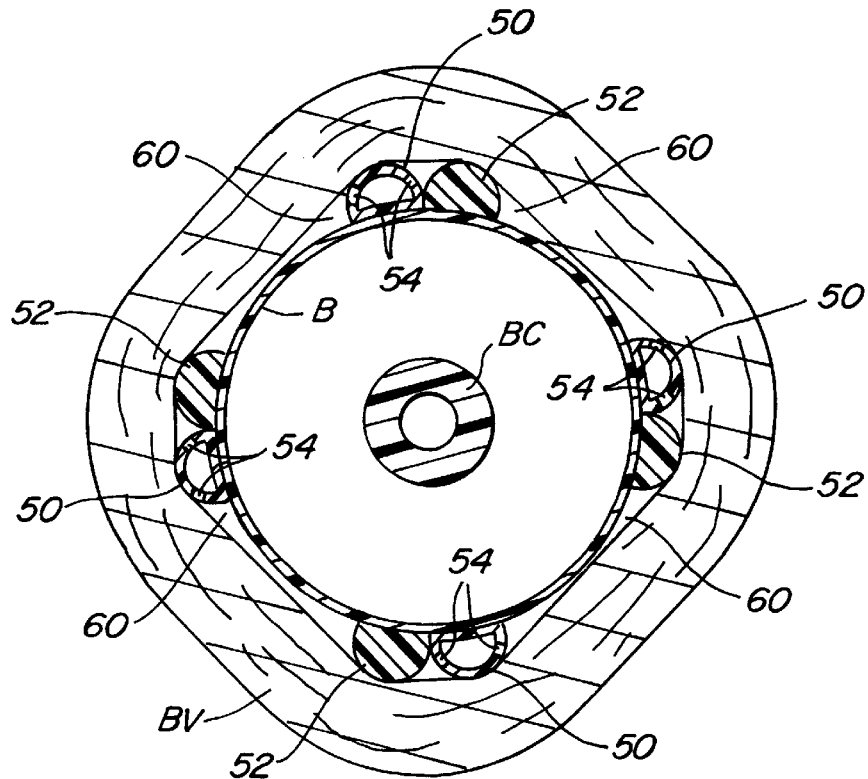
FIG. 13 is a cross-sectional view taken along line 13—13 of FIG. 11.
Figure 14:
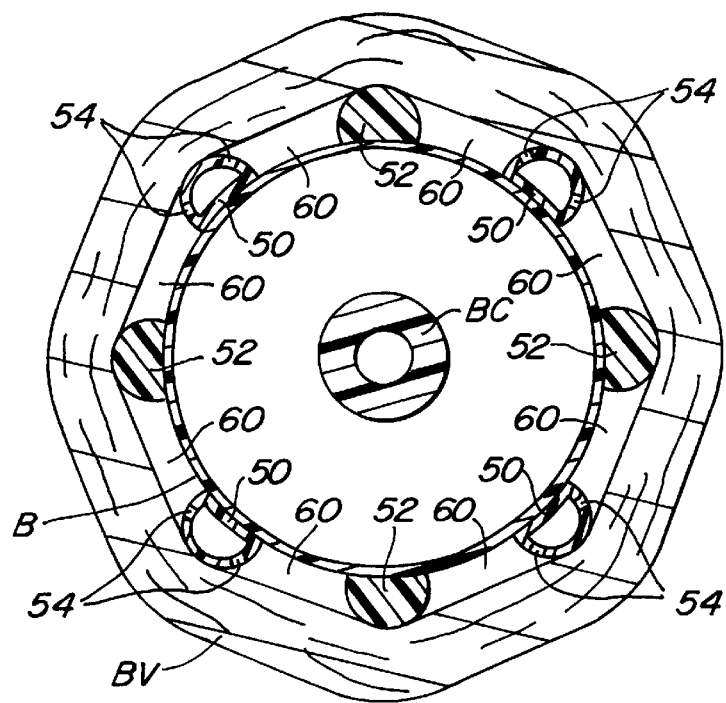
FIG. 14 is a cross-sectional view taken along line 14—14 of FIG. 11.

Referring now to FIGS. 11–14, the distal end of an alternative embodiment of a sleeve catheter constructed in accordance with the principles of the present invention comprises four infusion tubes 50 and four reinforcement ribs 52 arranged in an alternating pattern as best observed in the cross-sectional views of FIGS. 12–14. Each of the infusion tubes 50 include two rows of laterally disposed infusion ports 54 which are directed into reservoir pockets 60 which are formed when the tubes 50 and ribs 52 are radially expanded by a balloon B, as best seen in FIGS. 11, 13, and 14. The reservoir pockets 60 are formed between the outer peripheral surface of the expanded balloon B and an inner lumenal wall of the blood vessel BV, with the limits (peripheries) of the pockets being defined by the adjacent infusion tubes 50 and reinforcement ribs 52. The reinforcement ribs 50 serve to enhance the pushability of the sleeve catheter 49 when it is positioned relative to the balloon catheter.

The infusion ports will preferably be disposed adjacent only to pockets which are fully isolated, i.e. where the tubes 50 and ribs 52 are able to engage the arterial wall and seal the pocket. For example, it may be desirable to eliminate those ports adjacent pocket 55 since that pocket may not be entirely sealed when the balloon is fully inflated.

As seen in FIG. 12, the radially expansible portion of the catheter 49 of FIG. 11 is initially disposed over the balloon B of a conventional angioplasty catheter BC. In its radially collapsed configuration, each of the infusion tubes 50 and reinforcement ribs 52 will lie adjacent each other over substantially their entire lengths. The adjacent tubes 50 and ribs 52, however, will be attached to each other at discrete points in a manner similar to that described in connection with the catheter 10 of FIGS. 1–10. In particular, the attachment points will be axially staggered so that, upon inflation of balloon B, the infusion tubes 50 and reinforcement ribs 52 will circumferentially move apart in a controlled diamond-shaped pattern as seen in FIG. 11. Adjacent tubes 50 and ribs 52 will be attached to each other at particular locations as seen in the cross-section view of FIG. 13 taken along line 13—13 of FIG. 11. In contrast, the tubes 50 and ribs 52 will be unattached at different axial positions, as shown in the cross-sectional view of FIG. 14 taken along line 14—14 of FIG. 11. The distal ends of the tubes 50 and ribs 52 will typically terminate in a tapered atraumatic tip 58 as illustrated in FIG. 11.

The sleeve catheter embodiments described thus far can be deployed with either non-distensible or elastomeric (distensible) balloons. Conventional angioplasty balloons are typically formed from polyethyleneterephthalate which is a flexible but essentially non-distensible material. Thus, upon inflation to a relatively low threshold pressure of three or four atmospheres, the balloon will achieve its fully inflated diameter. Pressure increases above the threshold pressure will only marginally increase the balloon diameter, typically by no more than 15% for balloon inflation pressures up to about 12 atms. When used with such non-distensible balloons, the expansible portion of the sleeve catheter may have a fully expanded size slightly larger than that of the balloon. Over expansion of the balloon with the sleeve in place, however, can over distend the artery being treated. Thus, it is usually desirable to inflate the balloon to a pressure below the normal inflation pressure of the balloon alone.

When the sleeve catheter embodiments are expanded by elastomeric balloons, such as silicone rubber or latex balloons, the extent of balloon expansion will depend directly on the volume of incompressible fluid used for inflation. This type of expansion can automatically limit the pressure being applied to the artery wall. A reasonable amount of further balloon expansion will generally not increase the pressure against the artery wall, but will instead reduce the volume of the pockets defined by the sleeve catheter, the vessel wall, and the elastomeric balloon.

In the case of an elastomeric expansion balloon, the volume of the pocket reservoirs may typically also be reduced in comparison to the use of a non-distensible balloon. As seen in FIGS. 13 and 14, the fully expanded non-distensible balloon (or partially expanded elastomeric balloon) will tend to fall short of engaging the inner wall of the body lumen. When elastomeric balloons are used, they can be inflated sufficiently so that the balloon can approach and eventually engage the inner luminal wall along a portion of the length between adjacent infusion tubes and/or reinforcement ribs (not shown). Generally, the elastomeric balloons should not be inflated so that there is actual contact between the balloon and the vessel wall.

In addition to the use of both non-distensible and elastomeric balloons, use of the sleeve catheters described above can be varied by employing different types of membranes beneath the infusion tubes and reinforcement ribs. For example, the tubes and ribs can be supported over an elastomeric sleeve in order to control the underlying balloon expansion. Alternatively, the infusion tubes and reinforcement rods may be formed over a non-distensible membrane, mesh, or other containment pouch structures described above.

Figure 15:
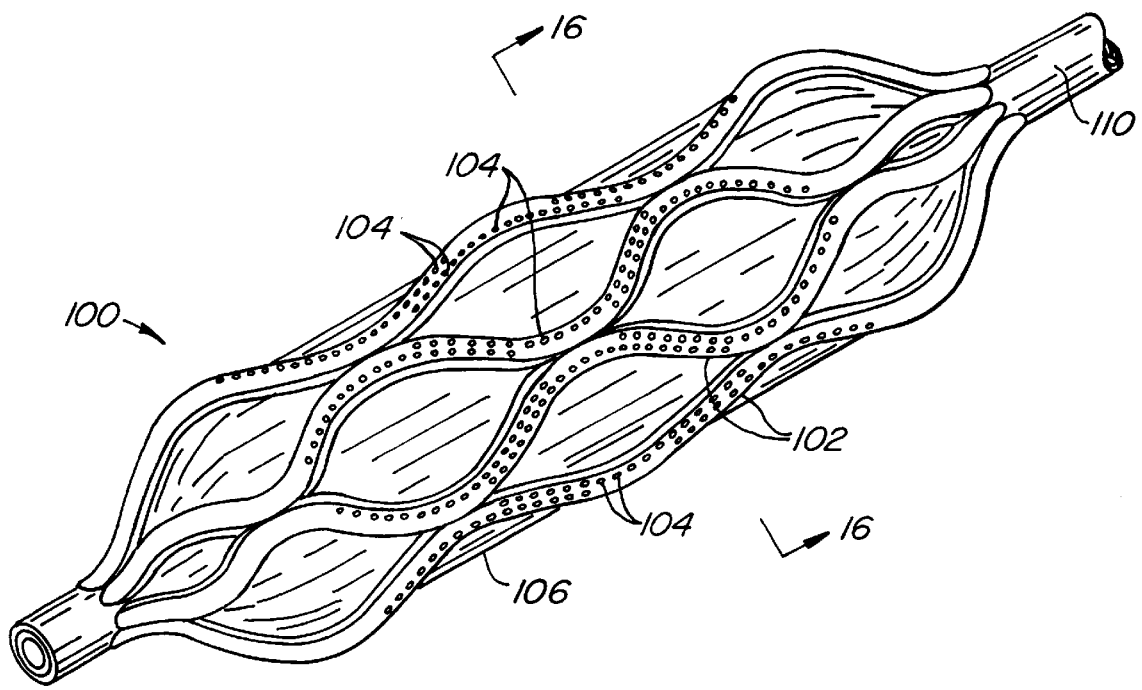
FIG. 15 illustrates an alternative construction of the catheter of the present invention, where the infusion tubes are integrally formed as part of an inflatable balloon on a balloon catheter.
Figure 16:
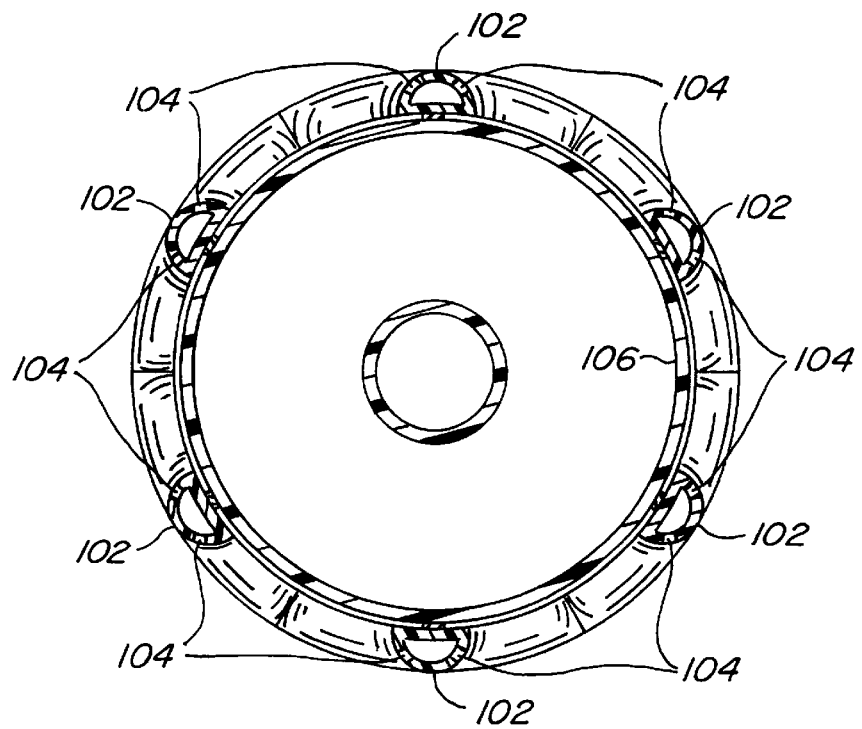
FIG. 16 is a cross-sectional view taken along line 16—16 of FIG. 15.

In addition to the sleeve catheter structures as discussed above, the methods of the present invention can be performed with modified balloon catheter constructions where the fluid infusion tubes are secured directly over an inflatable balloon, either a non-distensible balloon or an elastomeric balloon. Usually, infusion tubes will be formed separately from the balloon and attached by conventional means, such as adhesives, heat fusion, or the like. It will be possible to form the infusion tubes integrally with the balloons, although such integral structures will be very difficult to manufacture. An exemplary balloon catheter employing fluid infusion tubes according to the present invention is illustrated in FIGS. 15 and 16. A balloon 100 has a diamond-shaped arrangement of drug infusion tubes 102 formed over its outer peripheral surface. The tubes 102 have laterally disposed infusion ports 104 which direct fluid from their internal lumens into the pocket reservoirs therebetween. A fluid supply lumen will be arranged in the shaft of the catheter (not illustrated) to permit drug delivery to the infusion tubes from the proximal end of the catheter.

Figure 17:
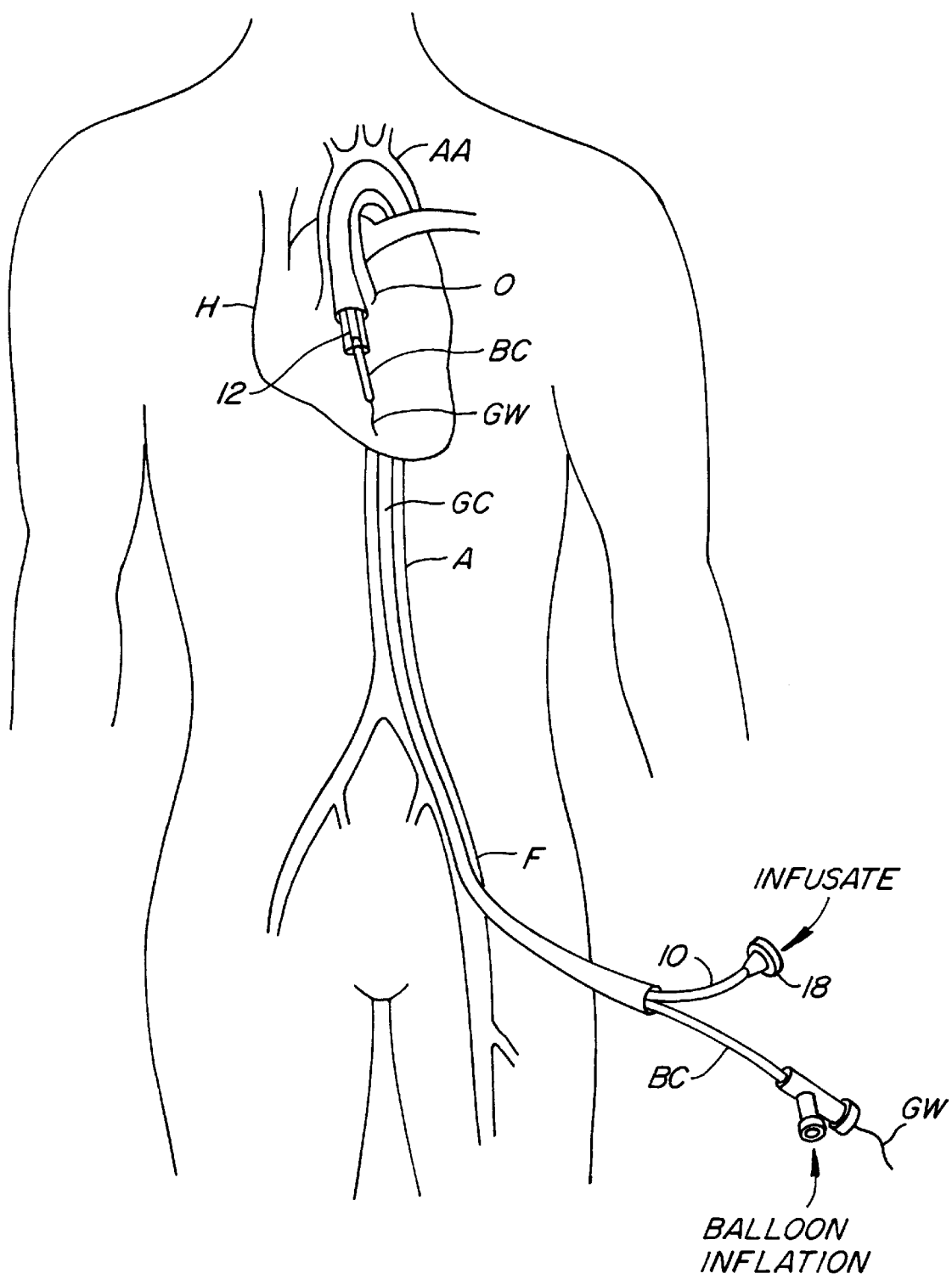
FIG. 17 illustrates the infusion catheter of FIG. 1 introduced together with a balloon angioplasty catheter through a guide catheter for treating a coronary artery according to the method of the present invention.

Referring now to FIG. 17, use of the sleeve catheter 10 of the present invention for delivering a desired fluid agent will be described. Infusion catheter 10 may be introduced through conventional guiding catheter GC to position the infusion sleeve 12 within a coronary artery in the patient's heart H, as illustrated in FIG. 17. Guiding catheter GC may be any conventional guiding catheter intended for insertion into the femoral artery F, then via the patient's aorta A around the aortic arch AA, to one of the coronary ostia O. Such guiding catheters are commercially available through a number of suppliers, including Medtronic, Minneapolis, Minn., available under the tradename Sherpa™. Specific guiding catheters are available for introducing catheters to either the left main or the right coronary arteries. Such guiding catheters are manufactured in different sizes, typically from 6F to 10F when used for coronary interventional procedures.

According to a method of the present invention, the balloon catheter BC is introduced through the balloon entry port 56, as described previously in connection with FIGS. 7–9. The atraumatic tip 19 of the infusion sleeve 12 will be positioned proximally of the balloon, typically by a distance in the range from 25 cm to 35 cm. The combination of the balloon catheter BC, and infusion catheter 10 will be introduced through the guiding catheter GC over a conventional guidewire GW until the balloon is positioned within the target site within the coronary artery. Preferably, the infusion sleeve 12 will remain positioned entirely within the guiding catheter GC while the balloon B of the balloon catheter BC is initially located at the target site. The balloon may then be expanded to treat the target site as well as other regions within the coronary vasculature in a conventional manner. After the angioplasty treatment is completed, the infusion sleeve 12 will be advanced distally over the balloon catheter BC until the radially expansible portion is properly positioned over the balloon. Such positioning can be confirmed by proper alignments of radiopaque markers on the infusion sleeve 12 (not shown) with markers on the balloon catheter, typically within the balloon itself. After the infusion sleeve is properly positioned, the balloon B on the balloon catheter BC will be inflated to engage the infusion tubes against the inner wall of coronary artery.

A desired infusate is then delivered through the hub 18 for desired treatment into the isolated pocket reservoirs 34, as described above. Typically, the infusate will be delivered at a flow rate from 0.1 ml/min to 40 ml/min, preferably from 1 ml/min to 20 ml/min. Infusion proximal pressures (measured at the proximal hub) will typically be in the range of 1 psi to 100 psi, preferably from 5 psi to 50 psi, with delivery pressures in the isolated reservoirs typically being 10 psi or below, usually being in the range from 0.5 psi to 10 psi. Balloon inflation pressures during infusion will typically be in the range from 0.5 atm to 6 atm, preferably from 1 atm to 2 atm for non-distensible balloons. For elastomeric (distensible) balloons, inflation will usually be controlled by volume rather than pressure, i.e. a sufficient volume of inflation medium will be delivered to fully expand the fluid reservoir pockets against the lumenal wall. Specific treatment pressures, times, and other conditions will depend on the nature of the infusate and condition being treated. Typically, treatment periods will not exceed 3 minutes, usually not exceeding 2 minutes, typically being in the range from 10 seconds to 3 minutes, in order not to occlude the blood vessel for a longer time than is tolerable to the patient without causing ischemia. Treatment protocols can be extended, however, by repetitively administering the infusate, i.e., deflating the balloon to reestablish coronary flow for a time sufficient to perfuse the distal coronary tissue and then re-inflating the balloon and delivering additional infusate. Such delivery steps can be repeated two, three, or more times as necessary to achieve a desired effect.

While the catheter 10 is useful for delivering fluid infusates to isolated fluid reservoirs according to the method of the present invention, certain advantages are obtained using the catheter embodiment of FIGS. 11–14. In particular, the use of laterally disposed infusion ports allows the reservoir pocket to be cleared of blood and other body fluids prior to drug delivery. For example, a vacuum may be applied to the fluid infusion lumen in order to remove the blood and other body fluids. In any case, the ultimate concentration of the drug can be enhanced by removing body fluids from the reservoirs prior to drug delivery.

Although the foregoing invention has been described in some detail by way of illustration and example, for purposes of clarity of understanding, it will be obvious that certain changes and modifications may be practiced within the scope of the appended claims.

What is claimed is:

1. A method for intramural fluid delivery, said method comprising:

expanding a balloon within a body lumen, said balloon having an outer peripheral surface;

providing a plurality of isolated fluid reservoir pockets between the outer peripheral surface of the balloon and an inner wall portion of the body lumen; and delivering fluid to said isolated pockets, wherein at least some of the individual reservoir pockets are surrounded by a continuous periphery of the infusion tubes which deliver fluid to the pockets.

2. A method as in claim 1, wherein the body lumen is a blood vessel.

3. A method as in claim 1, wherein from 6 to 64 isolated pockets are provided and wherein the isolated pockets each have an area in the range from 10 mm$^2$ to 60 mm$^2$.

4. A method as in claim 3, wherein the isolated pockets are substantially uniformly distributed over the outer peripheral surface of the balloon.

5. A method as in claim 1, wherein the balloon is inflated to a pressure in the range from 0.5 atm to 6 atm and wherein the fluid is delivered to said isolated pockets at a delivery pressure in the range from 0.5 psi to 10 psi.

6. A method as in claim 1, wherein the fluid is delivered to said isolated pockets from delivery lumens and through flow-limiting infusion ports, wherein the delivery lumens and flow-limiting infusion ports are present on a catheter which carries the balloon.

7. A method as in claim 6, wherein the flow-limiting infusion ports open to a single isolated pocket have an aggregate cross-sectional area which is from 5% to 20% of the cross-section area of the delivery lumen.

8. A method as in claim 1, wherein the providing step comprises disposing a network of fluid infusion tubes between the balloon and the inner wall portion, wherein the fluid infusion tubes are arranged to form said isolated pockets.

9. A method as in claim 8, wherein the fluid infusion tubes are arranged to form a diamond pattern when the balloon is expanded.

10. A method as in claim 8, wherein the network of fluid infusion tubes is disposed on an expansible sleeve which is positioned between the balloon and the luminal wall prior to balloon expansion.

11. A method as in claim 10, wherein the balloon is non-distensible.

12. A method as in claim 10, wherein the balloon is elastomeric.

13. A method as in claim 8, wherein the network of fluid infusion tubes is disposed as an integral component of the balloon.

14. A method as in claim 13, wherein the balloon is non-distensible.

15. A method as in claim 13, wherein the balloon is elastomeric.

16. An infusion catheter for intramural drug delivery within a body lumen, said infusion catheter comprising:

a catheter body having a proximal end, a distal end, and a fluid delivery lumen therethrough; and a radially expansible segment disposed at the distal end of the catheter body, said radially expansible segment having a network of fluid infusion tubes which are arranged to form a plurality of isolated pockets when said segment is expanded against a body lumen wall, said fluid infusion tubes having infusion ports for delivering fluids into said isolated pockets, wherein at least some of said isolated pockets are surrounded by a continuous periphery of infusion tubes when said pockets are disposed against a lumenal wall.

17. An infusion catheter as in claim 16, further comprising a balloon near the distal end of the catheter body, wherein the network of infusion tubes are formed over an outer peripheral surface of the balloon.

18. An infusion catheter as in claim 17, wherein the balloon is non-distensible and the infusion tubes are integrally formed therewith.

19. An infusion catheter as in claim 17, wherein the balloon is elastomeric and the infusion tubes are formed from a different material and attached to the balloon.

20. An infusion catheter as in claim 16, wherein the infusion ports opening to a single isolated pocket have an aggregate cross-sectional area which is from 5% to 20% of the cross-section area of the delivery lumen.

21. An infusion catheter as in claim 16, wherein the radially expansible segment comprises a receptacle which receives and is expanded by a balloon of a balloon catheter deployed therein.

22. An infusion catheter as in claim 16, wherein the network of infusion tubes forms from 6 to 64 isolated pockets disposed substantially uniformly over the expansible segment and wherein the isolated pockets each have an area in the range from 10 mm$^2$ to 60 mm$^2$.

23. An infusion catheter as in claim 16, wherein the fluid infusion tubes are arranged to form a diamond pattern when the expansible segment is expanded.

24. An infusion catheter as in claim 16, wherein the catheter body comprises a shaft having the fluid delivery lumen therethrough and wherein the radially expansible segment comprises a sleeve having the fluid infusion tubes formed thereover.

25. An infusion catheter as in claim 24, further comprising a manifold structure disposed between the shaft and the network of infusion tubes which distributes fluid from the fluid delivery lumen to the fluid infusion tubes.

26. An infusion catheter for use in combination with a balloon catheter, said infusion catheter comprising:

a catheter body having a proximal and a distal end;

a radially expansible sleeve disposed at the distal end of the catheter body, said radially expansible sleeve having a central receptacle, for receiving a balloon or the balloon catheter, and a network of fluid infusion tubes which are arranged to form a plurality of isolated pockets when expanded by the balloon present in the central receptacle, said fluid infusion tubes having infusion ports for delivering fluids into said isolated pockets, wherein at least some of said isolated pockets are surrounded by a continuous periphery of infusion tubes when said pockets are disposed against a lumenal wall.

27. An infusion catheter as in claim 26, wherein the catheter body comprises a shaft having a fluid delivery lumen therethrough.

28. An infusion catheter as in claim 27, further comprising a manifold structure disposed between the shaft and the network of infusion tubes which distributes fluid from the fluid delivery lumen to the fluid infusion tubes.

29. An infusion catheter as in claim 26, wherein the infusion ports opening to a single isolated pocket have an aggregate cross-sectional area which is from 5% to 20% of the cross-section area of the delivery lumen.

30. An infusion catheter as in claim 26, wherein the network of infusion tubes forms from 6 to 64 isolated pockets disposed substantially uniformly over the expansible segment and wherein the isolated pockets each have an area in the range from 10 mm$^2$ to 60 mm$^2$.

31. An infusion catheter as in claim 26, wherein the fluid infusion tubes are arranged to form a diamond pattern when the segment is expanded.

32. An infusion catheter for use in combination with a balloon catheter, said infusion catheter comprising:

a shaft having a proximal and a distal end and a fluid delivery lumen therethrough;

a radially expansible sleeve disposed at the distal end of the shaft, said radially expansible sleeve having a (i) central receptacle for receiving a balloon or the balloon catheter and (ii a network of fluid infusion tubes which are arranged to form a plurality of isolated pockets when the sleeve is expanded by the balloon present in the central receptacle, said fluid infusion tubes having infusion ports for delivering fluids into said isolated pockets; and a manifold structure disposed between the shaft and the network of infusion tubes which distributes fluid from the fluid delivery lumen to the fluid infusion tubes.

33. An infusion catheter as in claim 32, wherein the infusion ports opening to a single isolated pocket have an aggregate cross-sectional area which is from 5% to 20% of the cross-section area of the delivery lumen.

34. An infusion catheter as in claim 32, wherein the network of infusion tubes forms from 6 to 64 isolated pockets disposed substantially uniformly over the expansible segment.

35. An infusion catheter as in claim 32, wherein the isolated pockets each have an area in the range from 10 mm$^2$ to 60 mm$^2$.

36. An infusion catheter as in claim 32, wherein said radially expansible sleeve has reinforcing ribs within the fluid infusion tube network.

37. An infusion catheter as in claim 32, wherein the fluid infusion tubes are arranged to form a diamond pattern when the sleeve is expanded.

* * * * *